(12) United States Patent
Deshmukh

(10) Patent No.: US 8,864,786 B2
(45) Date of Patent: Oct. 21, 2014

(54) DUAL-LAYER MEDICAL BALLOON AND PROCESS OF MAKING

(75) Inventor: Susheel R. Deshmukh, Santa Rosa, CA (US)

(73) Assignee: Medtronic Vascular, Inc., Santa Rosa, CA (US)

(*) Notice: Subject to any disclaimer, the term of this patent is extended or adjusted under 35 U.S.C. 154(b) by 1125 days.

(21) Appl. No.: 12/421,167

(22) Filed: Apr. 9, 2009

(65) Prior Publication Data
US 2010/0262218 A1 Oct. 14, 2010

(51) Int. Cl.
| | | |
|---|---|---|
| A61M 29/00 | (2006.01) |
| A61L 29/14 | (2006.01) |
| A61F 2/958 | (2013.01) |
| A61L 29/08 | (2006.01) |
| A61M 25/10 | (2013.01) |
| B29C 47/00 | (2006.01) |
| B29C 47/06 | (2006.01) |
| B29C 47/26 | (2006.01) |
| B29C 49/04 | (2006.01) |
| B29K 21/00 | (2006.01) |
| B29K 77/00 | (2006.01) |
| B29L 31/00 | (2006.01) |

(52) U.S. Cl.
CPC .......... *A61L 29/141* (2013.01); *A61F 2/958* (2013.01); *A61L 29/085* (2013.01); *A61M 25/1029* (2013.01); *B29C 47/0023* (2013.01); *B29C 47/065* (2013.01); *B29C 47/26* (2013.01); *A61F 2240/001* (2013.01); *A61L 2420/08* (2013.01); *A61M 25/10* (2013.01); *A61M 25/104* (2013.01); *A61M 2025/1075* (2013.01); *B29C 49/04* (2013.01); *B29K 2021/00* (2013.01); *B29K 2077/00* (2013.01); *B29L 2031/7542* (2013.01)

USPC .................... 606/194; 604/103.06

(58) Field of Classification Search
USPC .......... 606/192, 194, 191; 604/96.01, 604/103.01–103.06
See application file for complete search history.

(56) References Cited

U.S. PATENT DOCUMENTS

| | | | |
|---|---|---|---|
| 5,116,318 A | 5/1992 | Hillstead | |
| 5,948,345 A | 9/1999 | Patel et al. | |
| 2002/0082553 A1* | 6/2002 | Duchamp | 604/103.06 |
| 2002/0165553 A1* | 11/2002 | Chin et al. | 604/523 |
| 2005/0043679 A1* | 2/2005 | Devens et al. | 604/103.06 |
| 2005/0266109 A1* | 12/2005 | Chin et al. | 425/133.5 |
| 2005/0288393 A1* | 12/2005 | Lean et al. | 523/201 |
| 2007/0142772 A1* | 6/2007 | Deshmukh et al. | 604/103.06 |
| 2008/0051541 A1* | 2/2008 | Strickler et al. | 526/265 |
| 2008/0065188 A1 | 3/2008 | Pallazza | |
| 2008/0114294 A1* | 5/2008 | Holman et al. | 604/96.01 |

FOREIGN PATENT DOCUMENTS

JP 06171043 A * 6/1994

OTHER PUBLICATIONS

Laura, DM, Keskkula, H, Barlow, JW, Paul, DR, "Effect of glass fiber and maleated ethylene-propylene rubber content on tensile and impact properties of Nylon 6," Polymer 41 (2000) 7165-7174.*

* cited by examiner

*Primary Examiner* — Katrina Stransky

(57) ABSTRACT

A dual-layer dilatation balloon, and a process of making such balloon, which includes an inner layer that includes a plasticizer and a polymer selected from the group consisting of a polyamide, a copolymer thereof, and a combination thereof, and an outer layer that includes an ethylene-propylene rubber. The dual-layer balloon optionally further includes a stent disposed on the balloon. The stent is optionally a drug-eluting stent.

22 Claims, 3 Drawing Sheets

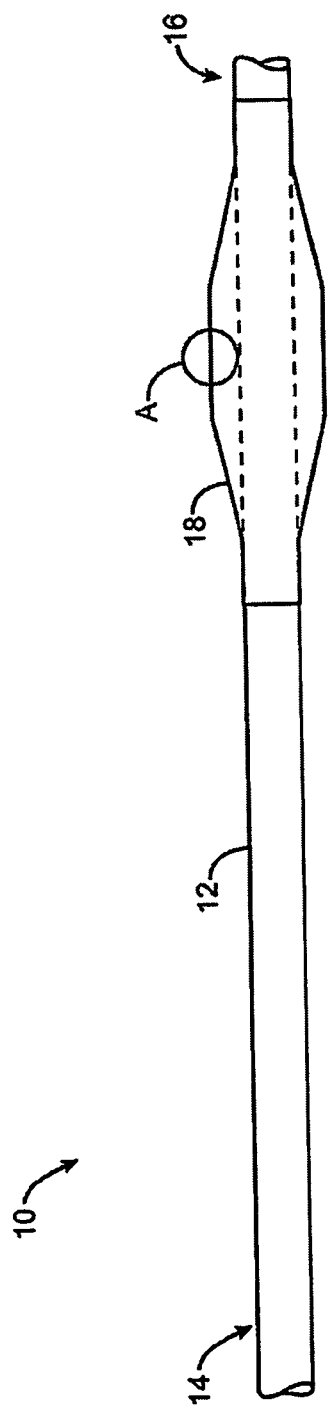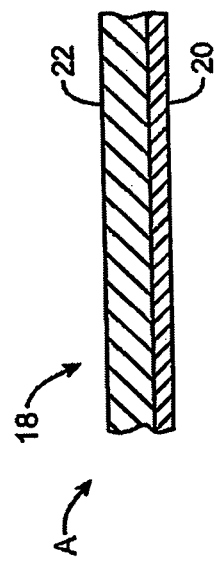

DUAL-LAYER MEDICAL BALLOON AND PROCESS OF MAKING

BACKGROUND OF THE INVENTION

Angioplasty balloons are typically produced by a combination of extrusion and stretch blow molding. The extrusion process is used to produce the balloon tubing, which essentially serves as a pre-form. This tubing is subsequently transferred to a stretch blow-molding machine capable of axially elongating the extruded tubing. Certain known processes involve blow-molding a balloon, in which a polymeric extrudate can be stretched in both radial and axial directions.

The materials used in balloons for dilatation are primarily thermoplastics and thermoplastic elastomers such as polyesters and their block co-polymers, polyamides and their block co-polymers, and polyurethane block co-polymers. For example, certain balloon materials include polyester-ether copolymers and polyether-polyamide copolymers. Dual-layer balloons are also known that include an inner layer that includes a polymer selected from the group consisting of a polyester, polyether, polyamide, and copolymers thereof, and an outer layer that includes a polyamide.

The unique conditions under which balloon dilatation is performed typically require extremely thin-walled, high-strength balloons that, when deflated, are flexible and trackable enough to be maneuvered through small, tortuous vessels. Balloons made from high-strength polymers, while exhibiting high burst strengths, exhibit less flexibility and trackability than desired. The addition of plasticizer to the materials increases the softness and flexibility of the balloon; however, the use of plasticizer can limit the balloons applicability as a bio-compatible material. Balloons that exhibit high burst strengths that can be used in stent delivery, but also exhibit high flexibility and trackability, are desired. New balloon materials are therefore needed to tailor the properties of the balloon and produce high-strength and highly flexible balloons for medical applications.

SUMMARY OF THE INVENTION

In one embodiment, the present invention relates to a dual-layer dilatation balloon including an inner layer that includes: a plasticizer and a polymer selected from the group consisting of a polyamide, a copolymer thereof, and a combination thereof; and an outer layer that includes a maleated ethylene-propylene rubber. The dual-layer balloon optionally further includes a stent disposed on the balloon. The stent is optionally a drug-eluting stent. Preferably, the dual-layer balloon has a hoop strength of 10,000 pounds per square inch (psi) to 60,000 psi.

In another embodiment, the present invention relates to a process for forming a dual-layer dilatation balloon. The process includes: forming a dual-layer extrudate; and forming the dual-layer balloon from the dual-layer extrudate in a balloon forming machine; wherein the balloon has a hoop strength of 10,000 psi to 60,000 psi. The dual-layer extrudate has an inner layer that includes: a plasticizer and a polymer selected from the group consisting of a polyamide, a copolymer thereof, and a combination thereof; and an outer layer that includes a maleated ethylene-propylene rubber.

In another embodiment, the present invention provides a balloon dilatation catheter, including a tubular elongated catheter shaft having proximal and distal portions, and a dual-layer dilatation balloon disposed oil the shaft. The balloon has an inner layer that includes: a plasticizer and a polymer selected from the group consisting of a polyamide, a copolymer thereof, and a combination thereof; and an outer layer that includes a maleated ethylene-propylene rubber. Optionally, the catheter includes a stent disposed on the balloon.

The terms "comprises" and variations thereof do not have a limiting meaning where these terms appear in the description and claims. The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention. As used herein, "a," "an," "the," "at least one," and "one or more" are used interchangeably. Thus, for example, "an" inner layer that includes "a" polyamide and "a" plasticizer can be interpreted to mean that "one or more" inner layers include "one or more" polyamides and "one or more" plasticizers. As used herein, the term "or" is generally employed in its sense including "and/or" unless the content clearly dictates otherwise. The term "and/or" means one or all of the listed elements or a combination of any two or more of the listed elements. As used herein, all numbers are assumed to be modified by the term "about" and preferably by the term "exactly." Notwithstanding that the numerical ranges and parameters setting forth the broad scope of the invention are approximations, the numerical values set forth in the specific examples are reported as precisely as possible. All numerical values, however, inherently contain certain errors necessarily resulting from the standard deviation found in their respective testing measurements. Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE DRAWINGS

FIG. 1 is a schematic side view of a balloon dilatation catheter according to an embodiment of the present invention;

FIG. 2 is a schematic detailed cross-sectional view of area A of FIG. 1;

DETAILED DESCRIPTION OF ILLUSTRATIVE EMBODIMENTS OF THE INVENTION

Figure 3:
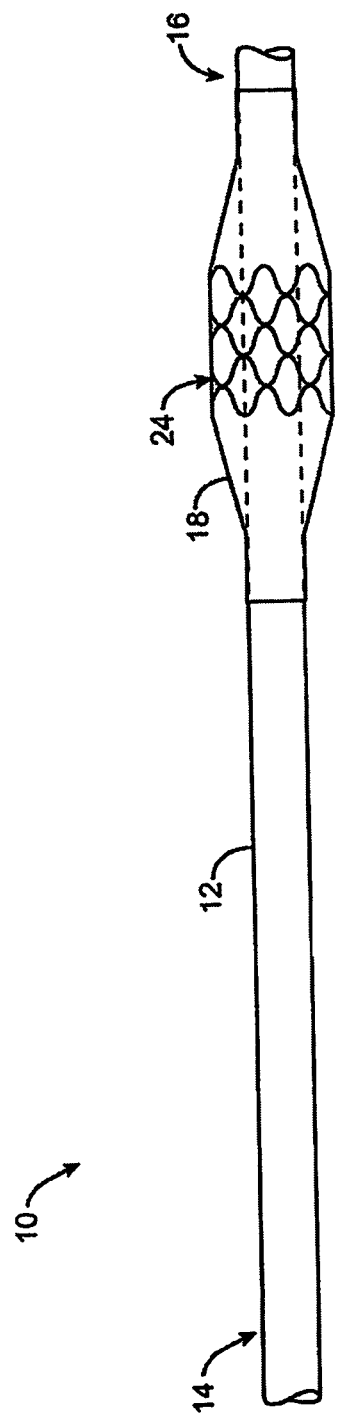
FIG. 3 is a schematic side view of a stent delivery catheter according to another embodiment of the present invention.

It is desirable to improve the flexibility and trackability of dilatation balloons while maintaining a high degree of strength in the balloon. Preferably, these improvements are made while using plasticizers, but limiting their ability to migrate out of the balloon. Improved flexibility and trackability would allow a surgeon to maneuver the balloon, and alternatively, a balloon and stent, through very small diameter vasculature that may have a large degree of blockage or plaque build-up. The high degree of strength provides the surgeon with maximum flexibility to inflate the balloon, and alternatively, to deliver a stent upon inflation, without bursting the balloon. In order to improve the flexibility of standard balloons with the use of plasticizer(s), the plasticizer is used in the inner layer of a dual-layer balloon with an outer layer that reduces and/or prevents the migration of the plasticizer(s) out of the inner layer.

A balloon dilatation catheter 10 (herein also referred to as "catheter") according to an embodiment of the invention is illustrated in FIG. 1. As illustrated, the catheter 10 includes a tubular elongated catheter shaft 12 (herein also referred to as "catheter shaft" or "shaft") having a proximal portion 14 and a distal portion 16, and a dual-layer dilatation balloon 18 (herein also referred to as "dual-layer balloon," "dilatation balloon," or "balloon") disposed on or otherwise connected to the distal portion 16 of the shaft 12.

With reference to FIG. 2, in one exemplary embodiment, the dual-layer dilatation balloon 18 includes an inner layer 20 that includes a plasticizer and polymer selected from the group consisting of a polyamide, a copolymer thereof, and a combination thereof, and an outer layer 22 that includes a maleated ethylene-propylene rubber.

Dilatation is used herein to refer to the expandability of the balloon. Balloons of the present invention are expandable 2% to 40% greater than the original balloon size. Preferably, the expandability of the balloon is in the range of 5% to 20%.

Hoop strength is directly related to the maximum amount of pressure the balloon can withstand, for a given wall thickness, without failing or bursting. The balloons of the present invention have high hoop strengths for their given wall thickness. High hoop strength is used herein to refer to balloons having double wall thicknesses in the range of 0.001 inch to 0.05 inch for the dual-layer, and having hoop strengths greater than 10,000 pounds per square inch (psi). Balloons of the present invention preferably have hoop strengths of 10,000 psi to 60,000 psi, alternatively, 20,000 psi to 50,000 psi, alternatively, 30,000 psi to 40,000 psi.

Polyamides for use in the inner layer 20 of balloon 18 of the present invention may include any polyamide that exhibits high hoop strength when formed into a dilatation balloon. Specific examples include, but are not limited to, nylon-type polyamides, such as, nylon-3, nylon-6, nylon-11, nylon-12, nylon-1/6, nylon-4/6, nylon-6/6, and nylon-6/10. A specific example includes, but is not limited to, Rilsan® AESNO polyamide 12 resin, available from Arkema, Inc. (Philadelphia, Pa.). Also included as a polymer of the inner layer 20 are copolymers of polyamides such as polyether block amides. Preferably, the number average molecular weight of the polyamide polymer and/or copolymer thereof used in the invention may be at least 5,000 Daltons, and preferably no more than 5,000,000 Daltons. The type of polyamide and/or copolymer thereof used in any particular balloon depends on several factors including, but not limited to, the type of polymer that will be co-extruded with the plasticizer, and the desired final properties of the balloon. Various combinations of polyamides and copolymers thereof can be used if desired.

The inner layer 20 of the dual-layer balloons 18 of the present invention further includes one or more plasticizers. Significantly, migration of the plasticizer from the inner layer 20 is reduced or eliminated by the outer layer 22 of the dual-layer balloon 18, which is desirable when used for delivery of a drug-eluting stent.

The term "plasticizer" is used herein to mean any material that can decrease the flexural modulus of a polymer. The plasticizer may influence the morphology of the polymer and/or may affect the melting temperature and/or glass transition temperature. Examples of plasticizers include, but are not limited to: small organic and inorganic molecules, oligomers and small molecular weight polymers (those having molecular weights (number average) less than 50,000 Daltons), highly-branched polymers and dendrimers. Specific examples include: monomeric carbonamides and sulfonamides; phenolic compounds; cyclic ketones; mixtures of phenols and esters; sulfonated esters or amides; N-alkylarylsulfonamides (e.g., N-ethyl-o-toluenesulfonamide, N-ethyl-p-toluenesulfonamide, and N-butylbenzenesulfonamide); selected aliphatic diols; phosphite esters of alcohols; phthalate esters (e.g., diethyl phthalate, dihexyl phthalate, dioctyl phthalate, didecyl phthalate, di(2-ethylhexy) phthalate, and diisononyl phthalate); alcohols (e.g., glycerol, ethylene glycol, diethylene glycol, triethylene glycol, oligomers of ethylene glycol, 2-ethylhexanol, isononyl alcohol, isodecyl alcohol, sorbitol, and mannitol); ethers (e.g., oligomers of polyethylene glycol, including PEG-500, PEG-1000 and PEG-2000); and amines such as triethanol amine. Preferred plasticizers include N-alkylarylsulfonamides (e.g., N-ethyl-o-toluenesulfonamide, N-ethyl-p-toluenesulfonamide, and N-butylbenzenesulfonamide). Various combinations of plasticizers can be used if desired.

The outer layer 22 of the dual-layer balloon 18 according to embodiments of the present invention includes a maleated ethylene-propylene rubber (EPR), which may or may not include other monomers such as in a maleated ethylene-propylene-diene rubber. Any maleated ethylene-propylene rubber can be used as the outer layer 22. Preferably, the number average molecular weight is at least 12,000 Daltons, and preferably no more than 80,000 Daltons. A specific example includes, but is not limited to, maleic anhydride functionalized elastomeric ethylene copolymer available under the trade designation EXXELOR™ VA 1803 from ExxonMobil Chemical Co. (Houston, Tex.). Various combinations of such polymers can be used if desired.

The dual-layer balloons 18 of the present invention optionally further include one or more additives (other than one or more plasticizers as discussed above). Additives can be used in the inner layer 20, the outer layer 22 (e.g., outer polyamide layer) or in both layers. The term "additive" is used herein to refer to any material added to the polymer to affect the polymer's and/or the balloon's properties. Examples of additives for use in the invention include fillers, antioxidants, colorants, crosslinking agents, impact strength modifiers, drugs and biologically active materials, and combinations thereof.

With reference to FIG. 3, the dual-layer balloons 18 of the present invention optionally further include a stent 24 disposed on the balloon 18. The dual-layer balloons 18 have high hoop strengths and allow for expanded delivery of the stent upon inflation of the balloon without bursting or puncturing the balloon. The stent 24 optionally includes a drug or biologically active material. Any drug or biologically active material can be used in the stent. Specific examples include, but are not limited to, corticosteroids, such as dexamethasone, immunosuppressants, such as everolimus, sirolimus, and tacrolimus, zotarolimus, and chemotherapeutic agents, such as paclitaxel. The drug or biologically active material elutes out of the stent and into the surrounding tissue over a controlled and predictable time.

Figure 4:
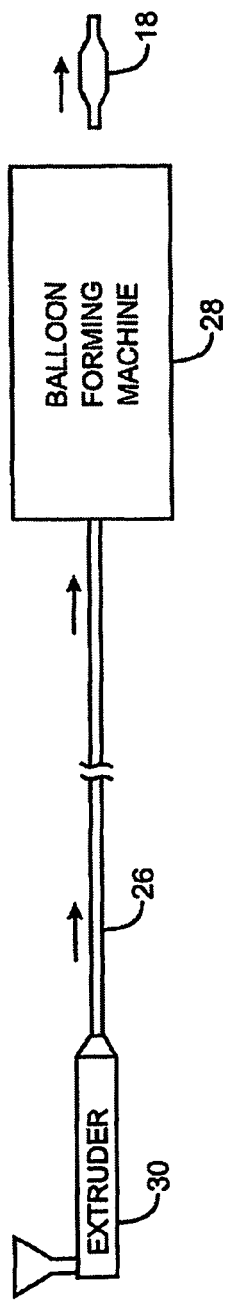
FIG. 4 is a schematic drawing of a process for forming a dual-layer dilatation balloon according to an embodiment of the present invention.

In another embodiment, the present invention relates to a process for forming a dual-layer dilatation balloon, which is schematically depicted in FIG. 4. The process includes forming a dual-layer extrudate 26 (herein also referred to as "extrudate") including an outer layer including an ethylene-propylene rubber (e.g., a maleated ethylene-propylene rubber) and an inner layer including a plasticizer and a polymer selected from the group consisting of a polyamide, a copolymer thereof, and a combination thereof. The dual-layer balloon 18 is then formed from the dual-layer extrudate 26 in a balloon forming machine 28, such that the balloon has hoop strength of 10,000 psi to 60,000 psi.

The dual-layer extrudate 26 may be formed in a tubular shape using an extruder 30. Extruders for use in the present invention include any extruder capable of forming dual-layer, tubular-shaped articles. Examples of extruders include, but are not limited to, single screw and double or twin screw thermoplastic extruders. In one embodiment, the material used for the outer layer polymer and the inner layer polymer are loaded into different hoppers on the extruder in pellet or flake form. The outer layer polymer and inner layer polymer are then extruded in different barrels, and co-extruded through a die, at which point, the two layers come together to form the dual-layer tubular extrudate 26. Preferably, no bonding layer is used and the dual-layer extrudate 26 is formed as a single article.

The extrusion temperature depends on the actual polymers being extruded. In general, the extrusion is performed at a temperature sufficient to melt the polyamide and inner layer polymers. For example, when extruding nylon 12, as the inner layer, and maleated EPR as the outer layer, the extruder may be heated such that the temperature of extrusion is typically at least 120° C. and preferably at least 135° C., and typically no greater than 315° C. and preferably no greater than 300° C. Tubular is used herein to mean a hollow, cylindrical-shaped article having an inner diameter, an inner circumference, an outer diameter and an outer circumference.

After forming the tubular extrudate 26, which may also be referred to as a parison or preform, the extrudate 26 is further processed in a balloon-forming step. The balloon-forming step is performed according to any one of the methods known to one of skill in the relevant art, such as a stretch blow-molding process. In one example, the stretching method of U.S. Pat. No. 5,948,345 to Patel et al. can be used. According to the method of Patel et al., a length of tubing including a biaxially orientable polymer(s) or copolymer(s) is first provided having first and second portions with corresponding first and second outer diameters. Also provided is a mold 32 that defines an internal cavity having a generally cylindrical shape.

Figure 5:
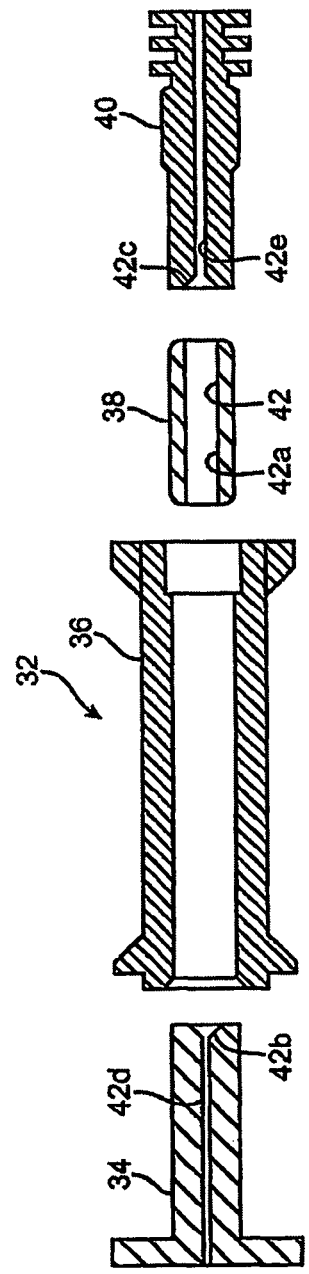
FIG. 5 is a detailed cross-sectional view of an embodiment of a mold for forming the dual-layer dilatation balloon of the present invention.

As shown in FIG. 5, the mold 32 includes a first portion 34, a second portion 36, a third portion 38, and a fourth portion 40. The first portion 34, third portion 38, and fourth portion 40 are configured to be inserted into the second portion 36 in an abutting relationship so that the inner surfaces of the first portion 34, third portion 38, and fourth portion 40 define the balloon forming surface 42. The balloon forming surface 42 includes a central cylindrical portion 42a, defined by the third mold portion 38, and tapered portions 42b, 42c and neck portions 42d, 42e, defined by the first portion 34 and the fourth portion 40, as shown in FIG. 5. In an embodiment, the outer diameter of the extrudate 26 is larger than the diameter defined by the neck portion 42d of the first mold portion 34, and is smaller than the diameter of the neck portion 42e of the fourth portion 40, as well as the diameter of the central cylindrical portion 42a. The central cylindrical portion 42a may be sized relative to the outer diameter of the extrudate 26 so that the desired orientation and increase in hoop strength in the sidewall of the balloon 18 may be obtained.

To form the balloon 18, for example, the extrudate 26 may be placed in the mold 32 and heated above the glass transition temperatures of the polymers in the two layers 20, 22. Pressure may then be applied to the extrudate 26 and the extrudate 26 may be longitudinally stretched such that it expands radially during the stretching. The extrudate 26 may be stretched, for example, 4 to 7 times the length of its original length. In an embodiment, a pressure of 300 psi to 500 psi may be applied. A second higher pressure, 0.15% to 40% higher than the first pressure, may then be applied, and the resulting balloon 18 may be finally cooled below the glass transition temperatures of the polymers. One skilled in the relevant art appreciates that much of the stretching process can be performed by automated equipment in order to lower per unit costs. Upon completion of the stretching, the balloon 18 may be attached to the distal portion 16 of the catheter shaft 12 by known methods to complete the production of the balloon dilatation catheter 10.

After forming, the dual-layer balloon 18 of embodiments of the present invention may have a double wall thickness of, for example, 0.001 inch to 0.004 inch, and a diameter of 2 millimeters (mm) to 5 mm. Double wall thickness is typically measured across a deflated, flat balloon. In the case of a dual-layer balloon such as balloon 18, double-wall thickness is actually a measurement of four thicknesses, i.e. four layers of material. In one embodiment, the thickness of the inner layer 20 is typically one-quarter to one-third of the thickness of the outer layer 22. In one example, the inner layer 20 has a thickness of 0.0004 inch to 0.003 inch and the outer layer 22 has a thickness of 0.0005 inch to 0.015 inch (and preferably, 0.0013 inch). In another embodiment, the dual-layer balloon 18 may be made in accordance with the present invention having diameter of 3.5 mm, a double wall thickness of 0.0017 inch, and a burst strength of 315 psi.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A dual-layer dilatation balloon comprising:
    an inner layer comprising a plasticizer and a polymer selected from the group consisting of a polyamide, a copolymer thereof, and a combination thereof;
    an outer layer comprising a maleated ethylene-propylene rubber and a drug or biologically active material;
    wherein the maleated ethylene-propylene rubber reduces and/or prevents migration of the plasticizer out of the inner layer to thereby reduce and/or prevent contact between the plasticizer and the drug or biologically active material.

2. The balloon of claim 1, wherein said inner layer comprises a nylon polymer.

3. The balloon of claim 2, wherein the nylon polymer comprises nylon-3, nylon-6, nylon-11, nylon-12, nylon-1/6, nylon-4/6, nylon-6/6, or nylon-6/10.

4. The balloon of claim 1, wherein the copolymer of a polyamide comprises a polyether block amide.

5. The balloon of claim 1, wherein the balloon has a hoop strength of 10,000 psi to 60,000 psi.

6. The balloon of claim 1, wherein the outer layer comprises a maleated ethylene-propylene-diene rubber.

7. The balloon of claim 1, wherein the plasticizer comprises a carbonamide, sulfonamide, phenolic compound, cyclic ketone, mixture of phenols and esters, sulfonated ester, sulfonated amide, N-alkylarylsulfonamide, aliphatic diol, phosphite ester of an alcohol, phthalate ester, alcohol, ether, amine, or combinations thereof.

8. The balloon of claim 1, wherein one or both of said inner and outer layers further comprise at least one of a filler, antioxidant, colorant, crosslinking agent, impact strength modifier, or combinations thereof.

9. The balloon of claim 1, further comprising a stent disposed on said balloon.

10. The balloon of claim 9, wherein the stent is a drug-eluting stent comprising a drug or biologically active material.

11. A balloon dilatation catheter, comprising:
a tubular elongated catheter shaft having proximal and distal portions; and
a dual-layer dilatation balloon disposed on said shaft, wherein the balloon comprises:
an inner layer comprising a plasticizer and a polymer selected from the group consisting of a polyamide, a copolymer thereof, and a combination thereof;
an outer layer comprising a maleated ethylene-propylene rubber and a drug or biologically active material;
wherein the maleated ethylene-propylene rubber reduces and/or prevents migration of the plasticizer out of the inner layer to thereby reduce and/or prevent contact between the plasticizer and the drug or biologically active material.

12. The catheter of claim 11, further comprising a stent disposed on the balloon.

13. The catheter of claim 12, wherein the stent is a drug-eluting stent comprising a drug or biologically active material.

14. The catheter of claim 11, wherein the inner layer comprises a nylon polymer.

15. The catheter of claim 14, wherein the nylon polymer is nylon-3, nylon-6, nylon-11, nylon-12, nylon-1/6, nylon-4/6, nylon-6/6, or nylon-6/10.

16. The catheter of claim 11, wherein the copolymer of a polyamide comprises a polyether block amide.

17. The catheter of claim 11, wherein the balloon has a hoop strength of 10,000 psi to 60,000 psi.

18. The catheter of claim 11, wherein the outer layer comprises a maleated ethylene-propylene-diene rubber.

19. A process for forming a dual-layer dilatation balloon, comprising:
forming a dual-layer extrudate comprising:
an inner layer comprising a plasticizer and a polymer selected from the group consisting of a polyamide, a copolymer thereof, and a combination thereof; and
an outer layer comprising a maleated ethylene-propylene rubber; and
forming a dual-layer balloon from the dual-layer extrudate in a balloon forming machine;
adding a drug or biologically active material to the outer layer of the balloon;
wherein the balloon has a hoop strength of 10,000 psi to 60,000 psi; and
wherein the maleated ethylene-propylene rubber reduces and/or prevents migration of the plasticizer out of the inner layer to thereby reduce and/or prevent contact between the plasticizer and the drug or biologically active material.

20. The process of claim 19, wherein the copolymer of a polyamide comprises a polyether block amide.

21. The process of claim 19, wherein the outer layer comprises a maleated ethylene-propylene-diene rubber.

22. A balloon dilatation catheter, comprising:
a tubular elongated catheter shaft having proximal and distal portions; and
a dual-layer dilatation balloon disposed on said shaft, wherein the balloon comprises:
an inner layer comprising a plasticizer and a polymer selected from the group consisting of a polyamide, a copolymer thereof, and a combination thereof;
an outer layer comprising a maleated ethylene-propylene rubber; and
a drug-eluting stent disposed on said balloon, wherein said drug-eluting stent comprises a drug or biologically active material;
wherein the outer layer reduces and/or prevents migration of the plasticizer out of the inner layer to thereby reduce and/or prevent contact between the plasticizer and the drug or biologically active material.

* * * * *